United States Patent [19]
Wade et al.

[11] 3,940,398
[45] Feb. 24, 1976

[54] 2-[[4-(AZINE OR DIAZINE OR TRIAZINE)-1-PIPERAZINYL]ALKYL]-1H-BENZ[DE]ISOQUINOLINE-1,3(2H)-DIONES

[75] Inventors: Peter C. Wade, Pennington, N.J.; Berthold Richard Vogt, Yardley, Pa.

[73] Assignee: E. R. Squibb & Sons, Inc., Princeton, N.J.

[22] Filed: Jan. 23, 1975

[21] Appl. No.: 543,558

[52] U.S. Cl. .................. 260/268 TR; 260/249.5; 260/256.4 C; 260/256.4 N; 424/249; 424/250; 424/251
[51] Int. Cl.² .................................. C07D 401/14
[58] Field of Search ... 260/268 TR, 256.4 N, 249.5, 260/256.4 C; 424/250, 249, 251

[56] References Cited
UNITED STATES PATENTS
3,247,208  4/1966  Schenker ......................... 260/281

Primary Examiner—Richard J. Gallagher
Assistant Examiner—Jose Tovar
Attorney, Agent, or Firm—Lawrence S. Levinson; Merle J. Smith; Stephen B. Davis

[57] ABSTRACT

Compounds of the following formula and their acid addition salts

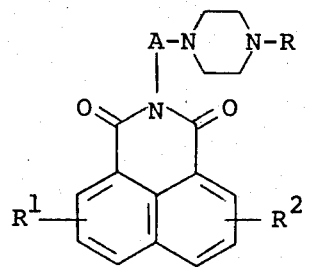

wherein R¹ and R² are independently selected from hydrogen, halogen, lower alkyl, lower alkoxy, lower alkylthio, nitro, cyano, amino and trifluoromethyl; A is a straight or branched chain alkylene of 1 to 8 carbons; and R is a 6-membered unsaturated substituted or unsubstituted heterocyclic ring selected from pyridine, diazine and triazine are disclosed. These compounds exhibit antidepressant activity. In addition these compounds are also useful as antiinflammatory agents.

12 Claims, No Drawings

2-[[4-(AZINE OR DIAZINE OR TRIAZINE)-1-PIPERAZINYL]ALKYL]-1H-BENZ-[DE]ISOQUINOLINE-1,3(2H)-DIONES

BACKGROUND OF THE INVENTION

Various naphthalimide compounds have been developed for use as dyes and optical brightening agents. Kimura et al., for example, at Chem. Abst., Vol. 62, 11950c, disclose N-[2-piperidinoethyl]-4-methoxy-1,8-naphthalimide (i.e. 6-methoxy-2-[2-(1-piperidinyl)ethyl]-1H-benz[de]isoquinoline-1,3(2H)-dione under the current Chem. Abst. nomenclature) as an optical brightening agent. Noguchi et al. in U.S. Pat. No. 3,625,947 disclose 2-[2-(2 or 4-pyridyl)ethyl]-1H-benz[de]isoquinoline-1,3(2H)-diones as fluorescent whitening agents.

Schenker et al. in U.S. Pat. No. 3,247,208 disclose that 1H-benz[de]isoquinoline-1,3(2H)-diones having a (1-substituted-4-piperidinyl) group in the 2-position possess anesthetic properties. Carron et al. in French Pat. No. 2,167,355 disclose that (4-phenyl)piperidine-2,6-diones having an alkylheteroalkyl substituent at the 1-position possess antidepressant activity. Imides having a nitroimidazolyethyl group as an N-substituent and possessing anti-bacterial and antiprotozoal activity are disclosed in U.S. Pat. Nos. 3,642,836 and 3,770,763 to Cusic et al. Certain imido dicarboxylic acid imides possessing various pharmacological properties are disclosed in U.S. Pat. No. 3,560,495 to Frankus et al.

Wu et al. in U.S. Pat. No. 3,717,634 and in the Journal of Med. Chem., Vol. 15, p. 477–479 (1972) disclose azaspirodecanediones having a [4-(pyridyl, primidinyl or triazinyl)-1-piperazinyl]alkylene group attached to the N atom which possess tranquilizing properties. Additionally, Wu et al. in U.S. Pat. Nos. 3,398,151 and 3,558,777 and in the Journal of Med. Chem., Vol. 12, p. 876–881 (1969) disclose azaspirodecanediones having a (4-phenyl-1-piperazinyl)-alkylene group attached to the N atom which possess various pharmacological activities including muscle relaxant and antiinflammatory activity and Mennear in U.S. Pat. No. 3,541,098 disclose 1,2-cyclobutanedicarboximides having a [4-(chlorophenyl)-1-piperazinyl]alkylene group attached to the N atom which possess central nervous system depressant activity and have useful analgesic and sedative properties.

SUMMARY OF THE INVENTION

This invention relates to new 2-[[4-(azine or diazine or triazine)-1-piperazinyl]alkyl]-1H-benz[de]isoquinoline-1,3(2H)-diones and their acid addition salts of the formula (I)

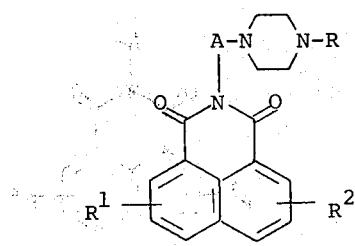

The symbols have the following meaning in formula I and throughout this specification.

$R^1$ and $R^2$ are each independently selected from hydrogen, halogen (preferably Br, Cl, or F), $CF_3$, lower alkyl, lower alkoxy, lower alkylthio, nitro, amino and cyano.

A is straight or branched chain alkylene of 1 to 8 carbons.

R is a 6-membered substituted or unsubstituted unsaturated heterocyclic ring selected from pyridine, diazine and triazine attached to the 4-position of the piperazinyl by way of a carbon atom. The terms diazine and triazine are meant to include the various isomeric forms, i.e. pyrimidine, pyridazine, pyrazine, s-triazine, a-triazine, and v-triazine. These rings can be substituted at one or two available carbon atoms by a lower alkyl, lower alkoxy, or halogen group.

DETAILED DESCRIPTION OF THE INVENTION

The various groups represented by the symbols have the meanings defined below and these definitions are retained throughout this specification.

The lower alkyl groups referred to throughout this specification include straight or branched chain hydrocarbon groups containing 1 to 4 carbons. Examples of the type of groups contemplated are methyl, ethyl, propyl, isopropyl, butyl, etc. The lower alkoxy groups include such lower alkyl groups attached to an oxygen, e.g., methoxy, ethoxy, propoxy, etc. The lower alkylthio group include such lower alkyl groups attached to a sulfur, e.g., methylthio, ethylthio, etc.

Straight or branched chain alkylene of 1 to 8 carbons is intended to include groups such as $-(CH_2)_n-$ wherein $n$ is 1 to 8,

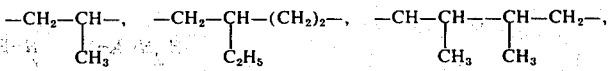

etc.

Preferred embodiments of this invention are as follows:

At least one of $R^1$ and $R^2$ is hydrogen and the other is hydrogen, Cl, F, Br, $CH_3$ or $OCH_3$.

R is 2-pyridinyl, substituted 2-pyridinyl, 2-pyrimidinyl, substituted 2-pyrimidinyl, 2,4,6-triazinyl and substituted 2,4,6-triazinyl wherein said substituent is a methyl, methoxy, or chlorine group attached to one or two available carbon atoms.

A is straight or branched chain alkylene of 1 to 6 carbons.

The most preferred compounds are:

$R^1$ and $R^2$ are both hydrogen. R is 2-pyridinyl. A is $-(CH_2)_n-$ wherein $n$ is an integer from 2 to 6.

The new compounds of this invention are prepared by the following reactions where A is straight or branched chain alkylene or 2 to 8 carbons.

The substituted naphthalic anhydride of formula II (II)

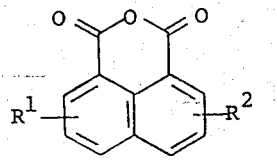

is reacted with an alkanolamine of formula III

H₂N—A—OH    (III)

to yield the alcohol of formula IV (IV)

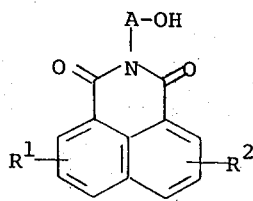

The alcohol of formula IV is converted to the intermediate of formula V (V)

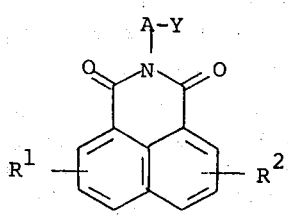

where Y is a leaving group such as tosylate, methanesulfonate or halogen by treating the alcohol with p-toluenesulfonyl chloride, methanesulfonyl chloride, thionyl chloride, thionyl bromide or hydrogen iodide.

The intermediate of formula V is then converted to the final products of formula I by reactions with compounds of the formula (VI)

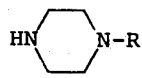

The compounds of formula VI can be prepared by the following reaction

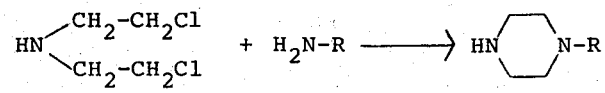

conducted at reflux temperature in an inert solvent such as toluene.

The substituted naphthalic anhydride of formula II can be converted directly to the final products of formula I by reacting the anhydride with compounds of formula VII (VII)   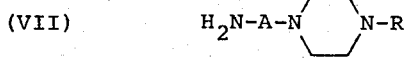

The following schematic summarizes the reactions described above.

where A is straight or branched chain alkylene of 2 to 8 carbons

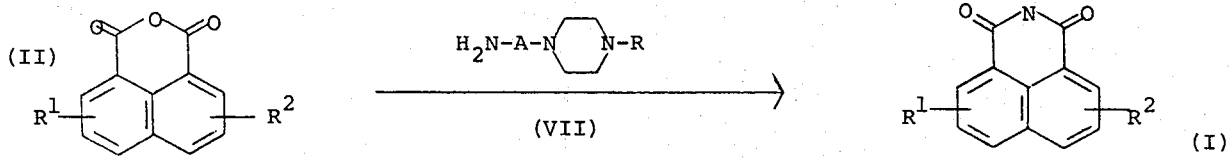

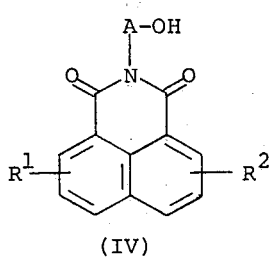

(IV)

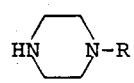

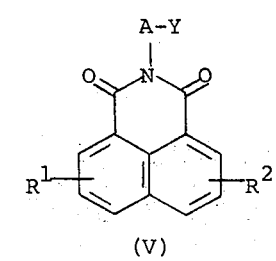

(V)

Also, the intermediate of formula V can be prepared by combining a substituted naphthalimide of formula VIII (VIII)

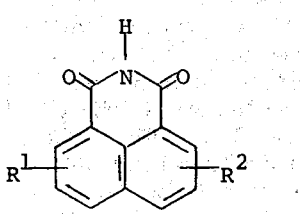

in an organic solvent with a polar organic solvent solution of a base, as for example an alcohol solution of potassium hydroxide, followed by the addition of a solution of the compound of formula IX, $$Y'-A-Y \quad (IX)$$

wherein Y' and Y are the same or different and are leaving groups selected from tosylate, methanesulfonate, or halogen and A is a straight or branched chain alkylene of 2 to 8 carbons.

Alternatively, the compounds of formula I wherein A is straight or branched alkylene of 2 to 8 carbons can be prepared by combining the anion of the substituted naphthalimide of formula VIII, described above, with a solution of the compound of formula X, (X) 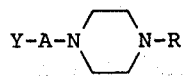

wherein Y is a leaving group as previously defined.

Also the compounds of formula I wherein A is straight or branched chain alkylene of 2 to 8 carbons can be prepared by reacting the intermediate of formula V with diethanolamine to form the intermediate

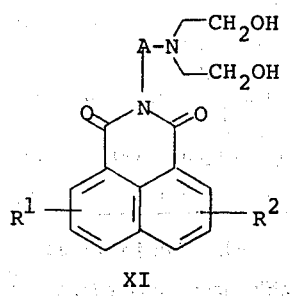

XI

This intermediate is then converted to the intermediate of formula XII where Y is a leaving group as defined previously by treating the alcohol with p-toluenesulfonyl chloride, methanesulfonyl chloride, thionyl chloride, thionyl bromide, hydrogen bromide or hydrogen iodide. The intermediate of formula XII can then be reacted as shown below to yield the final products of formula I Compounds of formula I where A is $-CH_2-$ are prepared by reacting the substituted naphthalimide of formula VIII suspended in a polar organic solvent such as dimethylformamide (DMF) with compounds of the formula VI and a source of formaldehyde such as aqueous formaldehyde or paraformaldehyde.

The various starting materials such as the substituted anhydrides of formula II, the alcohols of formula IV, the substituted naphthalimides of formula VIII, and the 4-substituted piperazines of formula VI, VII and X are known in the art or are readily obtainable by known procedures. Further process details are also provided in the illustrative examples.

The compounds of formula I wherein either or both $R^1$ and $R^2$ are amine are prepared by reducing the corresponding nitro substituted compound with a reducing agent such as hydrogen over a palladium catalyst or a suitable chemical reducing agent. This is preferably done as the last stage in the reaction procedures described above.

Depending on the reaction conditions and the starting materials used, the new compounds are obtained in the free form or in the form of their acid addition salts. The salts thereof can be converted into the free compounds in a known manner such as by reaction with a basic agent. Free bases which may be obtained can be converted into pharmaceutically acceptable acid addition salts by reaction with a variety of acids. Acids useful for preparing these acid-addition salts include, inter alia, inorganic acids, such as the hydrohalic acids (e.g. hydrochloric and hydrobromic acid), sulfuric acid, nitric acid, and phosphoric acid, and organic acids such as maleic, fumaric, tartaric, citric, acetic, benzoic, 2-acetoxybenzoic, salicyclic, succinic, nicotinic, methanesulfonic or cyclohexanesulfamic.

The new compounds of the present invention including the acid addition salts are capable of modifying the central nervous system. When administered to mice, cats, rats, dogs, and other mammalian species in amounts ranging from about 0.5 mg. to about 100 mg. per kg. of body weight per day, these compounds in particular exhibit antidepressant activity. A preferred dosage regimen for optimum results would be from about 1 mg. to about 50 mg. per kg. of body weight per day, and such dosage units are employed so that a total of from about 35 mg. to about 3 g. of active ingredient in single or divided doses are administered in a 24 hour period.

The antidepressant activity of the compounds of formula I is demonstrated by their ability to antagonize tetrabenzaine-induced ptosis according to the procedure of Vernier et al. ("The Pharmacodynamics of Amitriptyline", *Psychosomatic Medicine* , (1962), pages 683–690) and also by their ability to block the reuptake of monoamines in vitro according to the procedure of Horn et al. (*Molecular Pharmacology*, 7th Ed., (1971), page 66).

The compounds of formula I are also useful as antiinflammatory agents and may be used, for example, in a

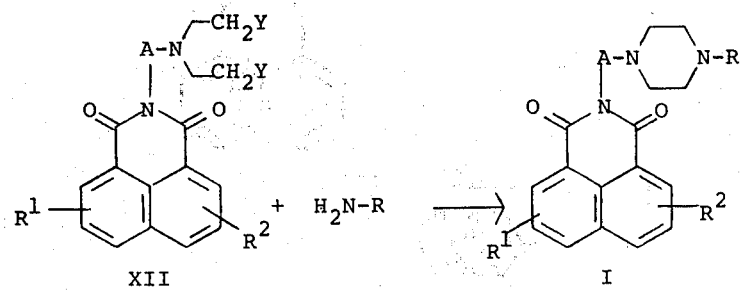

manner similar to phenylbutazone or indomethacin. They may be used to decrease joint swelling, tenderness, pain and stiffness in mammalian species, e.g., in conditions such as rheumatoid arthritis. The quantity administered ranges from about 1 mg. to about 30 mg. per kg. of body weight per day.

For any of these pharmaceutical purposes a compound or mixture of compounds of formula I or their pharmaceutically acceptable acid addition salts may be administered orally or parenterally in a conventional dosage form such as tablet, capsule, injectable or the like. These may be conventionally formulated in an oral or parenteral dosage form by compounding with a conventional vehicle, excipient, binder, preservative, stabilizer, flavor or the like as called for by accepted pharmaceutical practice.

The following examples are illustrative of the invention and represent preferred embodiments. Other modifications may be readily produced by suitable variations of the reactions. All temperatures are on the centigrade scale.

EXAMPLE 1

2-[2-[4-(2-Pyridinyl)-1-piperazinyl]ethyl]-1H-benz-[de]isoquinoline-1,3-(2H)-dione, hydrochloride (1:2)

a. 2-(2-Hydroxyethyl)-1H-benz[de]isoquinoline-1,3(2H)-dione

50 G. (0.252 mole) of naphthalic anhydride and 16 g. (0.262 mole) of ethanolamine are refluxed for three hours in 200 ml. of water (the solution is never complete). After cooling to 25° the water is decanted off and the residue recrystallized from 95% ethanol to yield 47.8 g. of 2-(2-hydroxyethyl)-1H-benz[de]isoquinoline-1,3(2H)-dione; m.p. 172°–173°.

b. 2-(2-Hydroxyethyl)-1H-benz[de]isoquinoline-1,3(2H)-dione, 4-methylbenzenesulfonate ester 52 G. (0.216 mole) of the 2-(2-hydroxyethyl)-1H-benz[de]isoquinoline-1,3(2H)-dione and 100 g. (0.525 mole) of p-toluenesulfonyl chloride are added to 600 ml. of pyridine previously cooled to 5°. The mixture is shaken briefly then allowed to stand overnight at 5°. The mixture is then poured into 3000 ml. of ice and water, stirred for 15 minutes and filtered. The insoluble material is stirred with fresh water, filtered off again and dried overnight at 25° (0.1 mm.) yielding 83 g. of 2-(2-hydroxyethyl)-1H-benz[de]isoquinoline-1,3(2H)-dione, 4-methylbenzenesulfonate ester.

c. 2-[2-[4-(2-Pyridinyl)-1-piperazinyl]ethyl]-1H-benz-[de]-isoquinoline-1,3(2H)-dione, hydrochloride (1:2)

10 G. (0.025 moles) of the ester from part (b), 4.1 g. (0.025 moles) of 1-(2-pyridinyl)piperazine and 3.27 g. (0.0253 moles) of diisopropylethylamine are refluxed in 300 ml. of toluene for 3.5 hours. The toluene is evaporated and the residue is dissolved in chloroform and washed with water (all aqueous layers are backwashed). The chloroform is evaporated and the residue is recrystallized from chloroform/ethanol to yield 2-[2-[4-(2-pyridyl)-1-piperazinyl]ethyl]-1H-benz-[de]isoquinoline-1,3(2H)-dione; m.p. 188°–190°.

This free base is dissolved in hot chloroform/ethanol and treated with excess alcoholic HCl causing the salt to precipitate. Recrystallization of this crude salt from methanol and methanol/ether followed by drying at 80° under a vacuum yields 4.0 g. of pure 2-[2-[4-(2-pyridinyl)-1-piperazinyl]-ethyl]-1H-benz[de]isoquinoline-1,3(2H)-dione, hydrochloride (1:2); m.p. 283°–284° (dec.).

EXAMPLES 2–12

Following the procedure of example 1 but substituting the alkanolamine shown in Col. I for the ethanolamine the following products are obtained wherein A is the radical shown in Col. II.

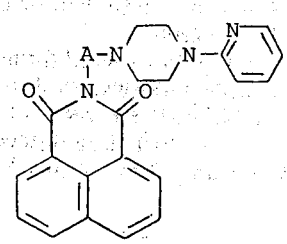

| Ex. | Col. I | Col. II |
|---|---|---|
| 2 | $H_2N-(CH_2)_3-OH$ | $-(CH_2)_3-$ |
| 3 | $H_2N-(CH_2)_4-OH$ | $-(CH_2)_4-$ |
| 4 | $H_2N-(CH_2)_5-OH$ | $-(CH_2)_5-$ |
| 5 | $H_2N-(CH_2)_6-OH$ | $-(CH_2)_6-$ |
| 6 | $H_2N-(CH_2)_7-OH$ | $-(CH_2)_7-$ |
| 7 | $H_2N-(CH_2)_8-OH$ | $-(CH_2)_8-$ |
| 8 | $H_2N-CH_2-CH(CH_3)-CH_2-OH$ | $-CH_2-CH(CH_3)-CH_2-$ |
| 9 | $H_2N-CH(CH_3)-(CH_2)_3-OH$ | $-CH(CH_3)-(CH_2)_3-$ |
| 10 | $H_2N-(CH_2)_3-CH(CH_3)-OH$ | $-(CH_2)_3-CH(CH_3)-$ |
| 11 | $H_2N-CH_2-CH(C_3H_7)-(CH_2)_2-OH$ | $-CH_2-CH(C_3H_7)-(CH_2)_2-$ |
| 12 | $H_2N-CH(CH_3)-CH_2-CH(CH_3)-OH$ | $-CH(CH_3)-CH_2-CH(CH_3)-$ |

EXAMPLES 13–44

Following the procedure of example 1 but substituting for the 1-(2-pyridinyl)piperazine the compounds shown in Col. I one obtains the products shown in Col. II wherein Het represents the radical shown below.

Col. I

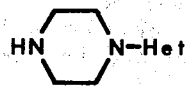

Ex.

13

Col. II

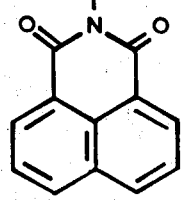

Het

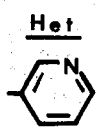

| Ex. | Het | Ex. | Het |
|---|---|---|---|
| 14 |  | 26 | 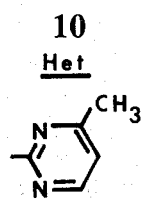 |
| 15 | 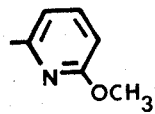 | 27 | 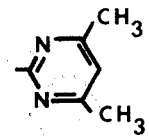 |
| 16 | 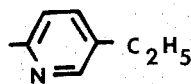 | 28 | 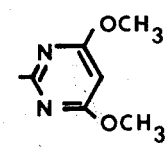 |
| 17 | 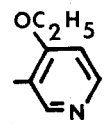 | 29 | 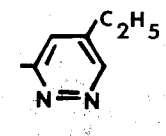 |
| 18 | 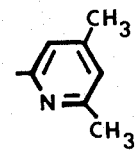 | 30 | 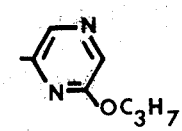 |
| 19 | 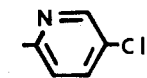 | 31 | 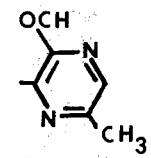 |
| 20 | 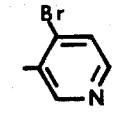 | 32 | 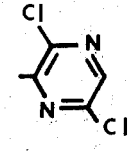 |
| 21 | 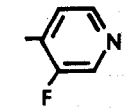 | 33 | 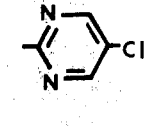 |
| 22 | 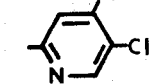 | 34 | 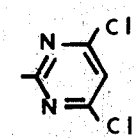 |
| 23 | 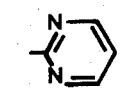 | 35 | 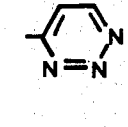 |
| 24 | 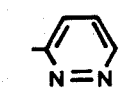 | 36 | 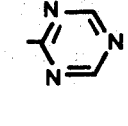 |
| 25 | 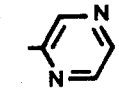 | 37 | 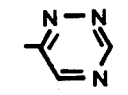 |

| Ex. | Het |
|---|---|
| 38 | 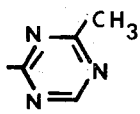 |
| 39 | 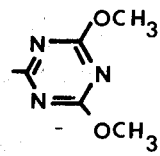 |
| 40 | 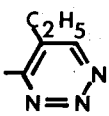 |
| 41 | 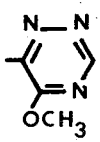 |
| 42 | 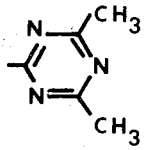 |
| 43 | 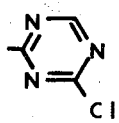 |
| 44 | 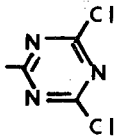 |

Similarly, by employing the substituted piperazines of examples 13 to 44 in the procedure of examples 2 to 12, other compounds within the scope of the invention are obtained.

EXAMPLE 45

2-[[4-(2-(Pyridinyl)-1-piperazinyl]methyl]-1H-benz-[de]isoquinoline-1,3(2H)-dione An equimolar mixture of 1-(2-pyridinyl)piperazine, aqueous formaldehyde, and 1,8-naphthalimide is suspended in a small amount of dimethylformamide and the mixture is heated until dissolution is complete. The solution is allowed to stand at room temperature and the resulting precipitate is filtered off and dried to yield 2-[[4-(2-pyridinyl)-1-piperazinyl]methyl]1H-benz-[de]isoquinoline-1,3(2H)-dione.

Similarly, by employing the substituted piperazines of examples 13 to 44 for the 1-(2-pyridinyl)piperazine in the above procedure, other compounds within the scope of the invention are obtained.

EXAMPLE 46

2-[4-[4-(2-Pyridinyl)-1-piperazinyl]butyl]-1H-benz-[de]isoquinoline-1,3(2H)-dione, hydrochloride (1:2)

a. 2-(4-Bromobutyl)-1H-benz[de]isoquinoline-1,3(2H)-dione

100 G. (0.5 mole) of 1,8-naphthalimide is suspended in 2100 ml. of dimethylformamide and the mixtrue is heated to 90° to form a complete solution. A solution of 36.3 g. (0.55 mole) of potassium hydroxide (85%) in 100 ml. of methanol is added resulting in the immediate formation of a yellow precipitate. The resulting mixture is stirred for one hour at 90° and cooled to 25°. 245 g. (1.0 mole) of 1,4-dibromobutane is added and the mixture is again heated to 90° and stirred for an additional hour. A precipitate remains in the mixture but is more granular than the initial material. The reaction mixture is cooled and the precipitate filtered off and discarded. The solvent is removed from the filtrate under vacuum and the residue is diluted with 500 ml. of hexane immediately precipitating crude 2-(4-bromobutyl)-1H-benz[de]isoquinoline-1,3(2H)-dione. The precipitate is filtered off, washed with fresh hexane and dried for 2 hours at 50° (0.1 mm.) to yield 2-(4-bromobutyl)-1H-benz[de]isoquinoline-1,3(2H)-dione. An analytically pure sample is prepared by dissolving the above product in hot 95% ethanol and recrystallizing by allowing the solution to cool to 25°. The resulting precipitate is dried for 2 hours at 50° (0.1 mm.) to yield pure 2-(4-bromobutyl)-1H-benz[de]isoquinoline-1,3(2H)-dione, m.p. 113°-115°.

b. 2-[4-[4-(2-Pyridinyl)-1-piperazinyl]butyl]-1H-benz-[de]-isoquinoline-1,3-(2H)-dione, hydrochloride (1:2)

9.0 G. (0.0271 mole) of 2-(4-bromobutyl)-1H-benz-[de]-isoquinoline-1,3(2H)-dione, 4.73 g. (0.0276 mole) of 1-(2-pyridinyl)piperazine, and excess sodium carbonate are refluxed in 200 ml. of benzene for 2 days. The sodium carbonate is filtered off and washed with hot chloroform. The organic portions are combined and evaporated and the residue is dissolved in toluene and washed with 10% HCl (twice). The combined acid washings are then washed with toluene and neutralized with KOH pellets. The resulting precipitate is extracted into chloroform, washed with water (twice), dried (Na₂SO₄), and evaporated. The residue is recrystallized from ethanol to yield 11.74 g. of 2-[4-[4-(2-pyridinyl)-1-piperazinyl]butyl]-1H-benz-[de]isoquinoline-1,3(2H)-dione; m.p. 150°-152°.

This free base is dissolved in dioxane and treated with 5N HCl in dioxane to precipitate 9.4 g. of 2-[4-[4-(2-pyridinyl)-1-piperazinyl]butyl]-1H-benz[de]isoquinoline-1,3(2H)-dione, hydrochloride (1:2); m.p. 280°-282°.

EXAMPLE 47

2-[5-[4-(2-Pyridinyl)-1-piperazinyl]pentyl]-1H-benz-[de]isoquinoline-1,3(2H)-dione, hydrochloride (1:2)

a. 2-(5-Bromopentyl)-1H-benz[de]isoquinoline-1,3(2H)-dione

Following the procedure of part (a) of example 46 but substituting 1,5-dibromopentane for the 1,4-dibromobutane, one obtains 2-(5-bromopentyl)-1H-benz[de]isoquinoline-1,3(2H)-dione; m.p. 113°–115°.

b. 2-[5-[4-(2-Pyridinyl)-1-piperazinyl]pentyl]-1H-benz[de]isoquinoline-1,3(2H)-dione, hydrochloride (1:2)

Following the procedure of part (b) of example 46 but substituting 2-(5-bromopentyl)-1H-benz[de]isoquinoline-1,3(2H)-dione for the 2-(4-bromobutyl)-1H-benz[de]isoquinoline-1,3(2H)-dione, one obtains 2-[5-[4-(2-pyridinyl)-1-piperazinyl]pentyl]-1H-benz[de]isoquinoline-1,3(2H)-dione, hydrochloride (1:2).

EXAMPLE 48

2-[6-[4-(2-Pyridinyl)-1-piperazinyl]hexyl]-1H-benz[de]isoquinoline-1,3(2H)-dione, hydrochloride (1:2)

a. 2-(6-Bromohexyl)-1H-benz[de]isoquinoline-1,3(2H)-dione

Following the procedure of part (a) of example 46 but substituting 1,6-dibromohexane for the 1,4-dibromobutane, one obtains 2-(6-bromohexyl)-1H-benz[de]isoquinoline-1,3(2H)-dione; m.p. 95°–96°.

b. 2-[6-[4-(2-Pyridinyl)-1-piperazinyl]hexyl]-1H-benz[de]isoquinoline-1,3(2H)-dione, hydrochloride (1:2)

Following the procedure of part (b) of example 46 but substituting 2-(6-bromohexyl)-1H-benz[de]isoquinoline-1,3(2H)-dione for the 2-(4-bromobutyl)-1H-benz[de]isoquinoline-1,3-(2H)-dione, one obtains 2-[6-[4-(2-pyridinyl)-1-piperazinyl]-hexyl]-1H-benz[de]isoquinoline-1,3(2H)-dione, hydrochloride (1:2).

Alternatively, the procedure of examples 46–48 can be employed to prepare the compounds of examples 1–44.

EXAMPLES 49–74

Following the procedure of example 1 but substituting for the 2-(2-hydroxyethyl)-1H-benz[de]isoquinoline-1,3(2H)-dione, 4-methylbenzenesulfonate ester the ester shown in Col. I one obtains the product shown in Col. II.

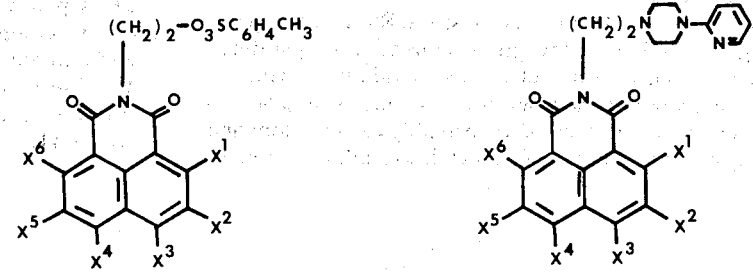

| Ex. | X¹ | X² | X³ | X⁴ | X⁵ | X⁶ |
| --- | --- | --- | --- | --- | --- | --- |
| 49 | H | H | Br | H | H | H |
| 50 | H | Cl | H | H | H | H |
| 51 | H | Br | H | H | H | H |
| 52 | H | F | H | H | H | H |
| 53 | H | I | H | H | H | H |
| 54 | H | Cl | H | H | Cl | H |
| 55 | Br | H | H | H | H | H |
| 56 | H | H | Cl | Cl | H | H |
| 57 | H | H | CH₃ | H | H | H |
| 58 | H | H | C₂H₅ | H | H | H |
| 59 | H | H | i-C₃H₇ | H | H | H |
| 60 | H | H | CH₃ | CH₃ | H | H |
| 61 | H | H | OCH₃ | H | H | H |
| 62 | H | H | OC₂H₅ | H | H | H |
| 63 | H | H | OC₃H₇ | H | H | H |
| 64 | H | H | OCH₃ | OCH₃ | H | H |
| 65 | H | NO₂ | H | H | H | H |
| 66 | H | H | NO₂ | H | H | H |
| 67 | H | CF₃ | H | H | H | H |
| 68 | H | H | CF₃ | H | H | H |
| 69 | H | CN | H | H | H | H |
| 70 | H | H | CN | H | H | H |
| 71 | H | H | NH₂ | H | H | H |
| 72 | H | NH₂ | H | H | H | H |
| 73 | H | SC₃H₇ | H | H | H | H |
| 74 | H | H | SCH₃ | H | H | H |

Similarly, by employing the ester of Col. I of examples 49–74 in the procedures of examples 13 to 44, other compounds within the scope of this invention are prepared. Similarly, by following the procedures of example 45 but employing a substituted 1,8-naphthalimide of formula VIII wherein the substituents are those listed under the headings $X^1$, $X^2$, $X^3$, $X^4$, $X^5$, and $X^6$ in examples 49 to 74, other compounds within the scope of this invention are prepared.

Also by following the procedure of examples 2–12, but employing a substituted 1,8-naphthalic anhydride of formula II wherein the substituents are those listed under the headings $X^1$, $X^2$, $X^3$, $X^4$, $X^5$ and $X^6$ in examples 49–74, other compounds within the scope of the invention are prepared.

What is claimed is:

1. A compound of the formula:

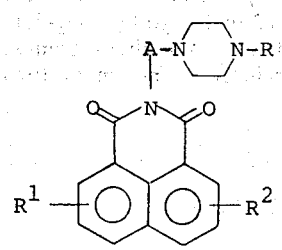

wherein $R^1$ and $R^2$ are each independently selected from the group consisting of hydrogen, halogen, lower alkyl, lower alkoxy, lower alkylthio, nitro, cyano, amino, and trifluoromethyl; A is a straight or branched chain alkylene of 1 to 8 carbons; and R is a heterocyclic ring selected from the group consisting of pyridinyl, diazine, triazine, and substituted pyridinyl, diazine, or triazine, wherein said heterocyclic ring is attached to the piperazine by way of an available carbon atom and said substituent is a lower alkyl, lower alkoxy, or halogen group attached to one or two available carbon atoms of said heterocyclic ring; or the pharmaceutically acceptable acid addition salts thereof.

2. The compound of claim 1 wherein at least one of $R^1$ and $R^2$ is hydrogen and the other is selected from the group consisting of hydrogen, Cl, Br, F, methyl and methoxy; A is a straight or branched chain alkylene of 1 to 6 carbons; and R is selected from the group consisting of 2-pyridinyl, 2-pyrimidinyl, 2,4,6-triazinyl, and substituted 2-pyridinyl, 2-pyrimidinyl, or 2,4,6-triazinyl wherein said substituent is a methyl, methoxy, or chlorine group attached to one or two available carbon atoms.

3. The compound of claim 1 wherein $R^1$ and $R^2$ are hydrogen; A is a straight chain alkylene of 2 to 6 carbon atoms; and R is 2-pyridinyl.

4. The compound of claim 3 wherein A is —(CH$_2$)$_2$—.

5. The compound of claim 4 having the name 2-[2-[4-(2-pyridinyl)-1-piperazinyl]ethyl]-1H-benz[de]isoquinoline-1,3(2H)-dione, hydrochloride (1:2).

6. The compound of claim 3 wherein A is —(CH$_2$)$_3$—.

7. The compound of claim 3 wherein A is —(CH$_2$)$_4$—.

8. The compound of claim 7 having the name 2-[4-[4-(2-pyridinyl)-1-piperazinyl]butyl]-1H-benz[de]isoquinoline-1,3(2H)-dione, hydrochloride (1:2).

9. The compound of claim 3 wherein A is —(CH$_2$)$_5$—.

10. The compound of claim 3 wherein A is —(CH$_2$)$_6$—.

11. A pharmaceutical composition consisting essentially of a compound or mixture of compounds of claim 1 and a pharmaceutically acceptable carrier.

12. The method of treating depression comprising administering an effective amount of the composition of claim 11.

* * * * *

UNITED STATES PATENT AND TRADEMARK OFFICE
CERTIFICATE OF CORRECTION

PATENT NO. : 3,940,398

DATED : February 24, 1976

INVENTOR(S) : Peter C. Wade et al

It is certified that error appears in the above-identified patent and that said Letters Patent are hereby corrected as shown below:

Col. 2, line 39, "$-CH-\underset{CH_3}{CH}-\underset{CH_3}{CH}-CH_2-$" should read
-- $-CH_2-\underset{CH_3}{CH}-\underset{CH_3}{CH}-CH_2-$ --.

Col. 2, line 60, "or" should read --of--.

Signed and Sealed this

Sixth Day of July 1976

[SEAL]

Attest:

RUTH C. MASON
Attesting Officer

C. MARSHALL DANN
Commissioner of Patents and Trademarks